(12) United States Patent
Balaj et al.

(10) Patent No.: US 9,829,483 B2
(45) Date of Patent: Nov. 28, 2017

(54) METHODS OF ISOLATING EXTRACELLULAR VESICLES

(71) Applicant: The General Hospital Corporation, Boston, MA (US)

(72) Inventors: Leonora Balaj, Charlestown, MA (US); Casey A. Maguire, Arlington, MA (US); Johan Skog, Charlestown, MA (US); Xandra O. Breakefield, Newton Center, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/023,913

(22) PCT Filed: Sep. 26, 2014

(86) PCT No.: PCT/US2014/057889
§ 371 (c)(1),
(2) Date: Mar. 22, 2016

(87) PCT Pub. No.: WO2015/048566
PCT Pub. Date: Apr. 2, 2015

(65) Prior Publication Data
US 2016/0216253 A1    Jul. 28, 2016

Related U.S. Application Data

(60) Provisional application No. 61/882,934, filed on Sep. 26, 2013.

(51) Int. Cl.
*A61K 9/127* (2006.01)
*G01N 33/53* (2006.01)
*G01N 33/566* (2006.01)
*G01N 33/543* (2006.01)
*G01N 1/40* (2006.01)

(52) U.S. Cl.
CPC ......... *G01N 33/5308* (2013.01); *A61K 9/127* (2013.01); *G01N 1/405* (2013.01); *G01N 33/5432* (2013.01); *G01N 33/566* (2013.01); *G01N 2400/40* (2013.01)

(58) Field of Classification Search
None
See application file for complete search history.

(56) References Cited

U.S. PATENT DOCUMENTS

2011/0064781 A1* 3/2011 Cleek ............... A61L 27/54
                                                      424/423
2011/0275078 A1* 11/2011 Pietrzkowski ...... C12Q 1/6809
                                                      435/6.11

OTHER PUBLICATIONS

International Search Report and Written Opinion dated Dec. 9, 2014 in International Application No. PCT/US2014/057889, 13 pgs.
Balaj et al., 751. Heparin affinity purification of extracellular vesicles from "Late Breaking Abstracts: Presented at the American Society of Gene & Cell Therapy's 16th Annual Meeting, May 15-18, 2013, Salt Lake City, Utah." Molecular Therapy 21.9 (2013): e1-46. Published online Sep. 6, 2013. p. e43-44.

* cited by examiner

*Primary Examiner* — Thomas S Heard
(74) *Attorney, Agent, or Firm* — Fish & Richardson P.C.

(57) ABSTRACT

The specification provides methods for isolating extracellular vesicles. Extracellular vesicles can be efficiently isolated, e.g., from biological fluids or cell culture media, using a heparin-coated solid support.

16 Claims, 15 Drawing Sheets

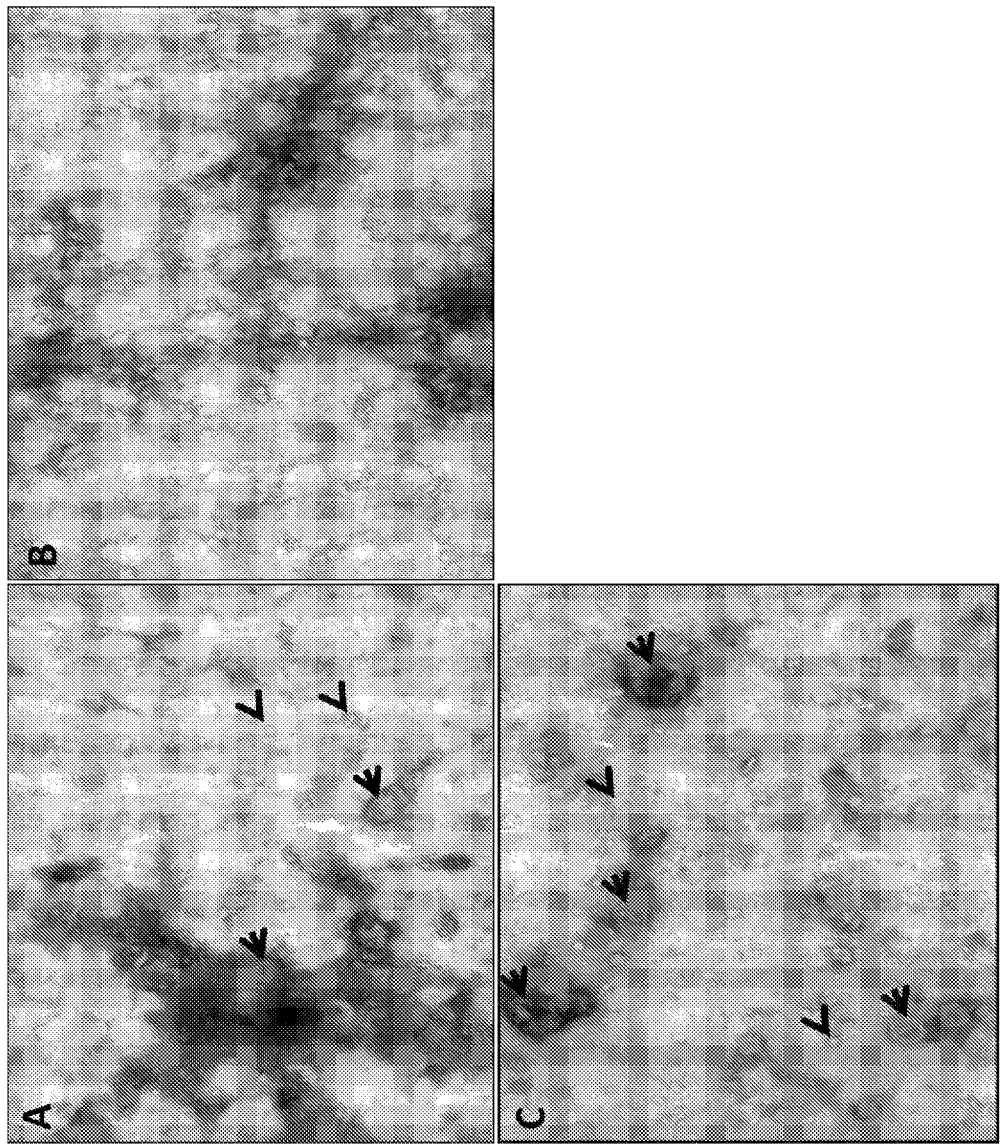
FIGs. 4A, 4B, and 4C

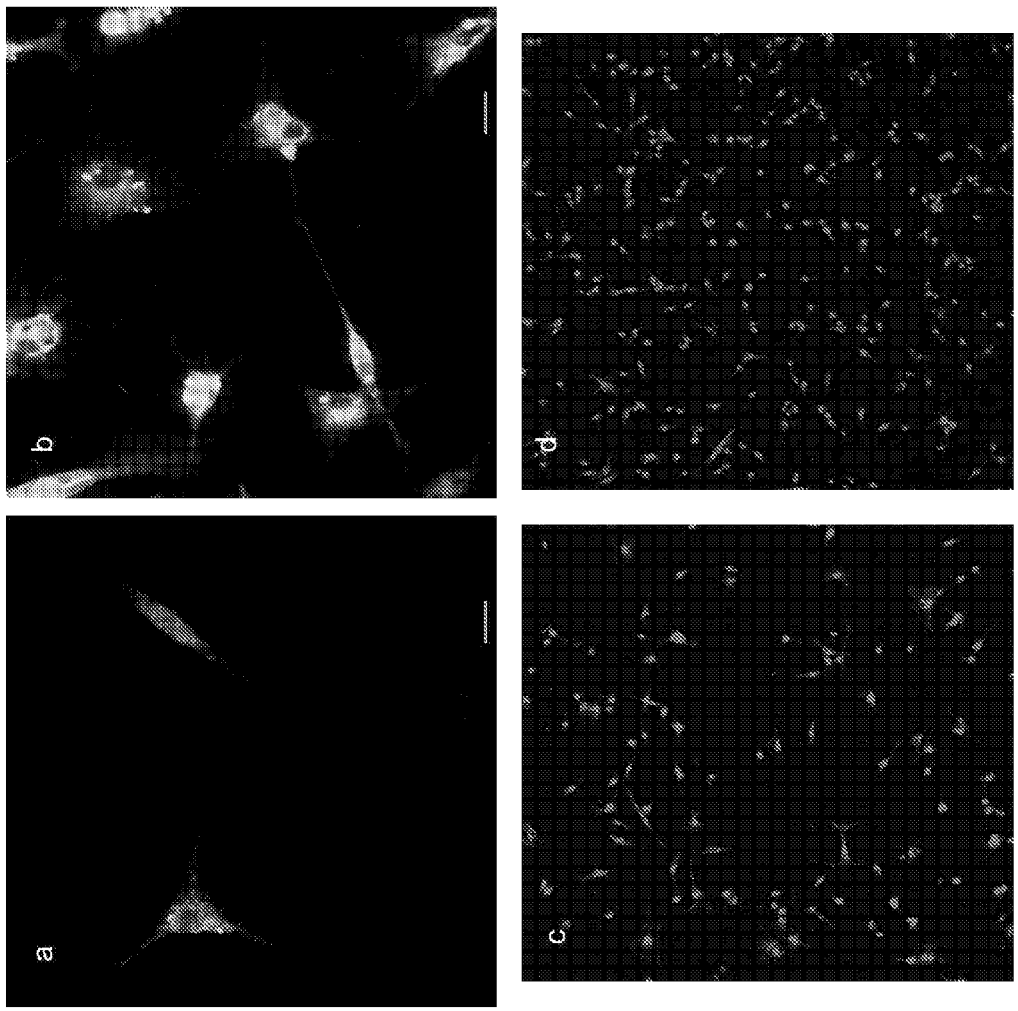
FIGs. 5A, 5B, 5C, and 5D

METHODS OF ISOLATING EXTRACELLULAR VESICLES

CLAIM OF PRIORITY

This application is a U.S. National Phase Application under 35 U.S.C. § 371 of International Patent Application No. PCT/US2014/057889, filed on Sep. 26, 2014, which claims the benefit of U.S. application Ser. No. 61/882,934, filed on Sep. 26, 2013, the contents of which are hereby incorporated by reference in their entirety.

STATEMENT AS TO FEDERALLY SPONSORED RESEARCH

This invention was made with U.S. Government support under Grant Nos. CA069246 awarded by the National Institutes of Health/National Cancer Institute and NS081374-01 awarded by the National Institutes of Health/National Institute of Neurological Disorders and Stroke. The Government has certain rights in the invention.

TECHNICAL FIELD

The claimed methods relate to isolating extracellular vesicles.

BACKGROUND

Extracellular vesicles (EVs) have been increasingly recognized as carriers of messages in cell-cell communication and biomarkers for different diseases, as well as for gene and drug delivery (Lee et al., Hum Mol Genet 21(R1):R125-34, 2012). EVs can be formed internally by invagination of the plasma membrane into endosomes, then in-budding of vesicles into endosomal-derived multivesicular bodies, and later fusion with the plasma membrane to release EVs into the intercellular surrounding (Thery et al., Nat Rev Immunol 9:581-593, 2009; Camussi et al., Kidney Int 78:838-848, 2010; Cocucci et al., Trends Cell Biol 19:43-51, 2009). EVs are also formed and released directly from the plasma membrane during cytoskeletal rearrangement, blebbing, or apoptosis (Camussi et al., Kidney Int 78:838-848, 2010). Cancer cells may also release a subpopulation of retroviral-like particles that are likely generated upon increased transcription of endogenous retroviral sequences (Contreras-Galindo et al., J Virol 82:9329-9336, 2008; Balaj et al., Nat Commun 2:180, 2011). Isolation and purification of released EVs remains a challenge. Methods currently used include differential and high speed ultracentrifugation (UC), separation on density gradients (Thery et al., Curr Protoc Cell Biol Chapter 3, Unit 3.22, 2006), proprietary commercial kits (e.g., EXOQUICK-TC™ kits), immune-affinity purification (Taylor et al., Methods Mol Biol 728:235-246, 2011; Tauro et al., Methods 56:293-304, 2012), and microfluidics (Chen et al., Lab Chip 10:505-511, 2010). UC, in addition to requiring specialized and expensive equipment, allows sedimentation of different types of EVs, including large oncosomes (Di Vizio et al., Cancer Res 69:5601-5609, 2009) and apoptotic bodies (Camussi et al., Kidney Int 78:838-848, 2010; Al-Nedawi et al., Cell Cycle 8:2014-2018, 2009) along with co-sedimentation of protein aggregates, such as BSA (Webber et al., J Extracell Vesicles doi: 10.3402/jev.v2i0.19861, 2013) and nucleic acids (Muller et al., J Immunol Methods 411C:55-65, 2014). Furthermore, EVs tend to cluster together and to form large aggregates in the pellet which are difficult to separate and may alter uptake of EVs by recipient cells (Momen-Heravi et al., Front Physiol 3:162, 2012). Density gradients are lengthy and laborious with low yield, and density may not be the best criteria to separate EVs, as it may vary significantly between samples. Other methods do not allow large scale EV isolation and/or require cocktails of disease-specific antibodies as well as lengthy optimizations. Therefore, there is a need for improved methods of efficiently isolating EVs.

SUMMARY

The present invention is based, in part, on the discovery that heparin can directly bind to the surface of EVs. Accordingly, the present invention features methods of isolating EVs. The methods include providing a sample comprising an EV, e.g., known or suspected to comprise an EV; contacting the sample with a heparin-coated solid support under conditions that allow the solid support to bind to the EV; and separating the solid support-bound EV from the sample, e.g., by centrifugation, elution, magnetization of the sample, decanting, thereby isolating the EV from the sample.

In some embodiments, the sample comprises biological fluid, e.g., human biological fluid. In one embodiment, the sample comprises urine, mucus, saliva, tears, blood, serum, plasma, sputum, cerebrospinal fluid, ascites fluid, semen, lymph fluid, airway fluid, intestinal fluid, breast milk, amniotic fluid, or any combination thereof. Alternatively, or in addition, the sample can comprise cell culture medium.

In one embodiment, the solid support is a bead, e.g., an agarose bead, a magnetic bead, a silica bead, a polystyrene plate, a polystyrene bead, a glass bead, a cellulose bead, or any combination thereof. In some embodiments, the solid support is a heparin-conjugated affinity chromatography column.

In one embodiment, the sample is contacted with the heparin-coated solid support at about 4° C., e.g., about 1° C., 2° C., 3° C., 5° C., 6° C., 7° C., 8° C., 10° C., 12° C., 14° C., 16° C., 18° C., 20° C., 22° C., 25° C., 26° C., 27° C., 28° C., 30° C., 32° C., 35° C., 38° C., or about 40° C. In some embodiments, the sample is contacted with the heparin-coated solid support for about or at least 30 minutes, e.g., about or at least 40 minutes, 45 minutes, 50 minutes, 55 minutes, 60 minutes, 70 minutes, 80 minutes, 90 minutes, 100 minutes, 120 minutes, 150 minutes, 180 minutes, 200 minutes, 210 minutes, 230 minutes, 240 minutes, 250 minutes, 260 minutes, 280 minutes, 300 minutes, 320 minutes, 380 minutes, 390 minutes, 400 minutes, 420 minutes, 440 minutes, 460 minutes, 480 minutes, 500 minutes, 520 minutes, 550 minutes, or about or at least 600 minutes. The support can optionally be washed to remove non-EV materials, and solid support-bound EVs can be separated from the sample, e.g., by centrifugation (of beads), e.g., at 10,000×g, 50,000×g, 100,000×g, or 200,000×g; by magnetization of the sample; or by other means, to isolate EVs.

In some embodiments, the solid support-bound EV is released from the solid support by incubating the solid support-bound EV with salt, e.g., sodium chloride, potassium chloride, magnesium chloride, and calcium chloride. The salt solution can be concentrated at about 1 M, 1.25 M, 1.5 M, 1.75 M, 2 M, 2.25 M, 2.5 M, 2.75 M, or about 6 M. In one embodiment, the solid support-bound EV is released from the solid support by incubating the solid support-bound EV with 2 M NaCl, in a buffer, e.g., phosphate-buffered saline at pH 7.2. In some embodiment, the solid support-bound EV is released from the solid support about 4° C., e.g., about 1° C., 2° C., 3° C., 5° C., 6° C., 7° C., 8° C., 10° C., 12° C., 14° C., 16° C., 18° C., 20° C., 22° C., 25° C., 26°

C., 27° C., 28° C., 30° C., 32° C., 35° C., 38° C., or about 40° C., for about or at least 30 minutes, e.g., about or at least 40 minutes, 45 minutes, 50 minutes, 55 minutes, 60 minutes, 70 minutes, 80 minutes, 90 minutes, 100 minutes, 120 minutes, 150 minutes, 180 minutes, 200 minutes, 210 minutes, 230 minutes, 240 minutes, 250 minutes, 260 minutes, 280 minutes, 300 minutes, 320 minutes, 380 minutes, 390 minutes, 400 minutes, 420 minutes, 440 minutes, 460 minutes, 480 minutes, 500 minutes, 520 minutes, 550 minutes, or about or at least 600 minutes. In on embodiment, the solid support-bound EV is released from the solid support by incubating the solid support-bound EV with heparinase at about 30° C., e.g., about 22° C., 25° C., 27° C., 29° C., 31° C., 33° C., 35° C., 37° C., or about 40° C., for about or at least 20 minutes, e.g., about or at least 25 minutes, 30 minutes, 35 minutes, 40 minutes, 45 minutes, 50 minutes, 55 minutes, 60 minutes, 70 minutes, 80 minutes, 90 minutes, 100 minutes, or about or at least 120 minutes.

In some embodiments, the methods include loading the isolated EV with a therapeutic agent, e.g., a siRNA, a miRNA, an antisense oligonucleotide, a polypeptide, a viral vector, or a drug.

In yet another aspect, kits for use in performing any one of methods described herein are provided. For example, the kits may contain at least one, e.g., two, three, five, or ten, solid supports described above. The kits can further include a solution comprising a buffer, e.g., PBS, preferably at a neutral pH, e.g., pH 7.2; a solution comprising high salt, e.g., 2 M or more concentrated salt, e.g., 1 M to 6 M or 2 M to 4 M, wherein the salt is NaCl, KCl, $MgCl_2$, $CaCl_2$, or other salt, in PBS (pH 7.2); and/or a solution comprising heparinase. In some embodiments, all of the solutions are nuclease free and/or sterile. In one embodiment, the kits include a filtration device, e.g., a 100 kDa molecular weight cutoff ultrafiltration device. In some instances, the kit may include one or more tubes, e.g., centrifuge or microcentrifuge tubes, e.g., a 50 mL centrifuge tube and/or a 1.5 mL microcentrifuge tube. In some embodiments, the 50 mL centrifuge tube and the 1.5 mL microcentrifuge tube are sterile and/or nuclease-free.

As used herein, "extracellular vesicles" or "EVs" are small circular cell membranes that range in size from about 20 to 1000 nm in diameter (or up to 5 μm for some EVs derived from tumor cells) and contain proteins, nucleic acids, lipids, and other molecules common to the originating cell. EVs secreted from cells include: (i) exosomes, which are vesicles having a diameter of about 20 to 100 nm that originate from cells; (ii) ectosomes (also called shedding microvesicles), which are vesicles that are released directly from plasma membranes and have a diameter of about 50 to 1000 nm; and (iii) apoptotic blebs, which are vesicles secreted from dying cells that have a diameter of about 50 to 5000 nm. The methods of the invention contemplate isolating any one or more of these EVs.

As used herein, "about" is used to indicate that a number, amount, time, etc., is not exact or certain but reasonably close to or almost the same as the stated value.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a schematic diagram showing an exemplary method to isolate and purify EVs with heparin-coated beads, e.g., agarose or magnetic beads, by incubating the beads with EVs released from a variety of cells lines (i), to yield bead-bound EVs (ii). Free floating proteins and nucleic acids are washed away with a buffer such as PBS (iii). Beads are then incubated overnight with a high salt wash, e.g., 2 M NaCl, and the EVs are released and collected by spinning down the beads and collecting the supernatant (iv). EVs are then collected and used as a source of DNA, RNA, proteins, lipids, and metabolites, or used in biological assays (v). FIG. 1B is a bar graph showing Nanoparticle Tracking Analysis (NTA) counts of heparin-isolated EVs eluted with 2 M NaCl overnight at 4° C. FIG. 1C is a bar graph showing NTA analysis of heparin beads incubated overnight with EVs, rinsed beads three times with PBS, and then mock-treated or treated with *Bacteroides* Heparinase I. FIG. 1D is a bar graph depicting NTA analysis of EVs that were pre-incubated or mock treated with heparin prior to isolation using the agarose heparin beads. FIG. 1E is a bar graph demonstrating that EV binding to beads is heparin-specific, and they do not bind to the agarose beads alone. FIG. 1F is a bar graph showing NTA counts from 293T-derived EVs isolated through two rounds of purification. FIGS. 1G and 1H are two bar graphs showing purification of EVs from other cell types using heparin beads. Human glioblastoma cell line U87 (FIG. 1G) and (FIG. 1H) human umbilical vein endothelial cells (HUVECs)-derived EVs were incubated with heparin beads, washed, and salt eluted. EV recovery was assessed as above. The data is presented as mean±s.d. (n=3).

FIG. 2A (top panel) is Coomassie stained protein gel revealing EV associated and co-pelleting proteins in each sample. The samples were also probed for the EV marker Alix (FIG. 2A, bottom panel; band indicated with black arrow). FIG. 2B is a series of four bioanalyzer graphs showing RNA yields and profiles from EVs extracted using the HeP, SuC, UC, and the commercial EXOQUICK-TC™ kit methods. FIG. 2C is a photomicrograph of an immunoblot to detect BSA in EV samples. FIG. 2D is a bar graph depicting qRT-PCR results when recovered RNA from each method was reverse transcribed into cDNA and used as input for the qRT-PCR. Levels of several genes were determined (x-axis). The data is represented as the average Ct values±s.d. (lower means higher levels of the gene) and normalized to the housekeeping gene GAPDH (n=3). p-values were calculated using the two-tailed t-test (*$p<0.05$, $p<0.01$, *$p<0.001$).

FIGS. 4A to 4C are a series of three photomicrographs from transmission electron microscopic examination of heparin-purified EVs. All preparations were isolated from one mL of concentrated conditioned media from 293T cells by ultracentrifugation (FIG. 4A), a commercial EXO-QUICK-TC™ kit (FIG. 4B), or heparin-coated beads (FIG. 4C). Scale bars=100 nm.

FIGS. 5A to 5C are a series of four photomicrographs showing that heparin-isolated EVs are functionally intact and are internalized into cells. 293T derived extracellular vesicles from (FIGS. 5A and 5C) ultracentrifuged and heparin-purified (FIGS. 5B and 5D) samples were labeled with the green fluorescent lipid dye (PKH67) and incubated with recipient U87 glioma cells to visualize internalization. Upper panels scale bar=10 μm.

DETAILED DESCRIPTION

Figure 1A:
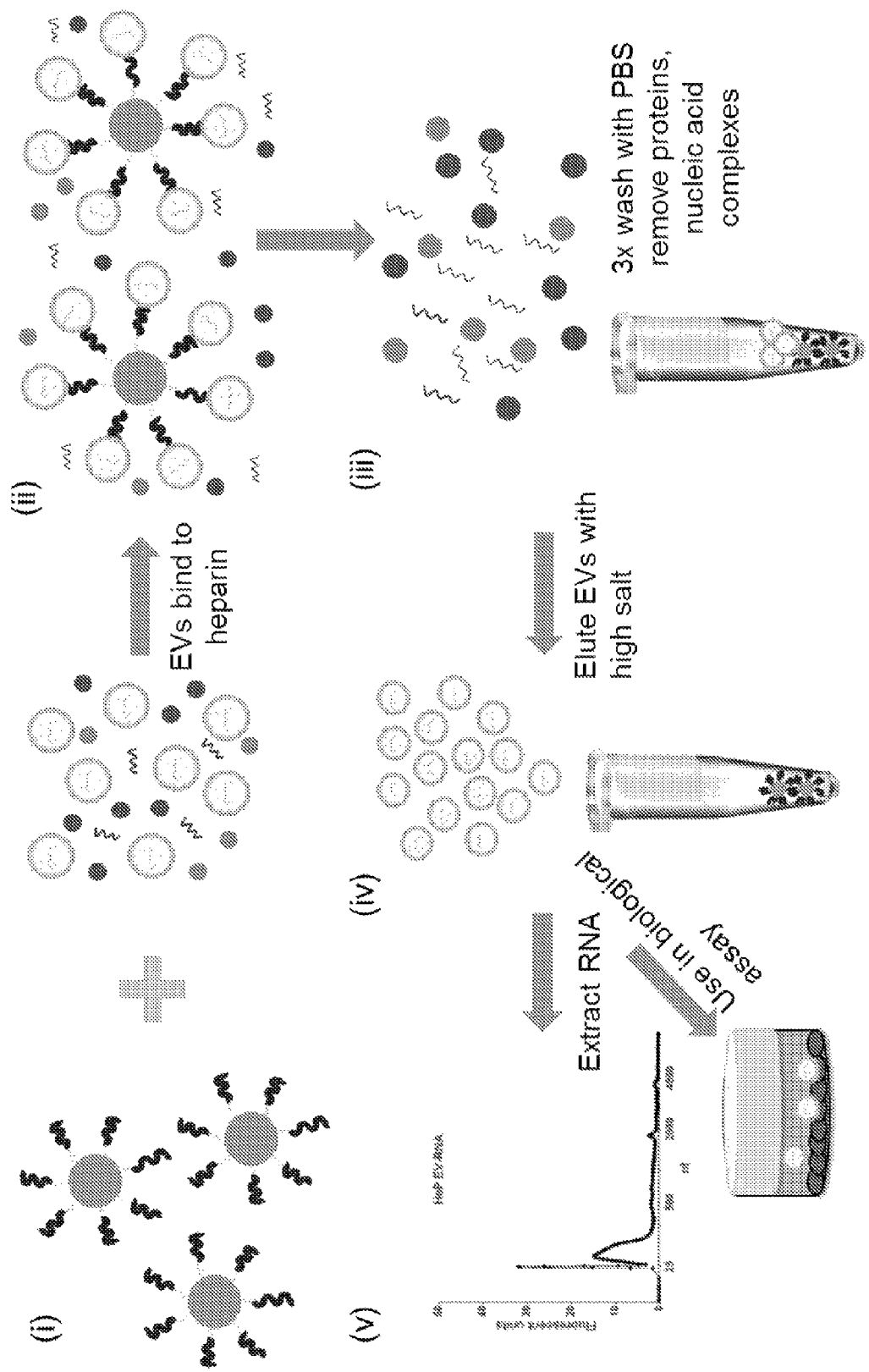
FIGS. 1A to 1H are a series of eight panels showing that EVs are efficiently isolated and purified using heparin-coated agarose beads.

The present disclosure provides methods to isolate or purify EVs from biological fluids, e.g., human urine, mucus, saliva, tears, blood, serum, plasma, sputum, cerebrospinal fluid, ascites fluid, semen, lymph fluid, airway fluid, intestinal fluid, breast milk, amniotic fluid, or any combination thereof, and cell culture medium. This disclosure is based at least in part on a series of experiments that used heparin to isolate a highly pure population of EVs from conditioned cell culture medium as well as blood serum and plasma. Heparin-purified EVs displayed the EV marker Alix, contained a diverse RNA profile, had low levels of bovine serum albumin contamination, and were functional at binding and uptake into recipient cells. Further, RNA yield was similar to isolation using UC.

Methods to Isolate EVs

Described herein are methods for rapidly isolating EVs from a sample, e.g., a liquid sample. Methods described herein employ a heparin-coated (which includes heparin-conjugated) solid support, e.g., a heparin-coated bead or plate such as an agarose bead, magnetic bead, silica bead, glass plate, polystyrene plate, polystyrene bead, glass bead, and cellulose bead, heparin-conjugated affinity chromatography columns, or any combination thereof. In some methods, the solid support is a streptavidin-coated magnetic bead, and biotinylated heparin is used to coat the streptavidin-coated magnetic beads, e.g., DYNABEADS® MYONE™ Streptavidin C1 (Life Technologies, Grand Island, N.Y.). Heparin is a highly-sulfated glycosaminoglycan with the highest negative charge density of any known biological molecule (Yang et al., Anal Bioanal Chem 399:541-557, 2011) and is primarily produced by mast cells (Powell et al., Glycobiology 14:17R-30R, 2004). There are various molecular weights of heparin ranging from about 5 to about 40 kDa with varying degrees of sulfation (negative charge). There are also heparin analogs that do not possess the anti-coagulant activity of heparin, structurally related heparan sulfate glycosaminoglycan, and other highly negatively charged compounds. Any one or more of these forms of heparin may be used for EV isolation.

In some embodiments, heparin in solution is used, and an anti-heparin antibody is used to put the EVs from solution, e.g., an anti-heparin antibody bound to a solid surface as described herein.

In some instances, the sample can be pre-cleaned or clarified before contact with the heparin by centrifugation and/or filtration and washed with a buffered solution, e.g., PBS, to remove cellular debris and proteins (some with heparin affinity) without loss of EVs. For example, the sample can be centrifuged at low speed, e.g., about 300×g, 1000×g, or 2000×g, to pellet debris. The sample can also be filtered to remove non-EV cellular debris by using, for example, a 50 kDa cutoff filter, a nanofiltration low-speed centrifugal device (e.g., Amicon Ultra-15 Centrifugal Filter Units) with a 50 kDa molecular weight cutoff filter, a 100 kDa cutoff filter, a 200 kDa cutoff filter, or a 500 kDa cutoff filter.

In these methods, a sample containing an EV is contacted with a heparin-coated solid support under conditions that allow the solid support to bind to the EV. The sample can be contacted with a heparin-coated solid support at about 4° C., e.g., about 1° C., 2° C., 3° C., 5° C., 6° C., 7° C., 8° C., 10° C., 12° C., 14° C., 16° C., 18° C., 20° C., 22° C., 25° C., 26° C., 27° C., 28° C., 30° C., 32° C., 35° C., 38° C., or about 40° C. The sample is contacted with the heparin-coated solid support for about or at least 30 minutes, e.g., about or at least 40 minutes, 45 minutes, 50 minutes, 55 minutes, 60 minutes, 70 minutes, 80 minutes, 90 minutes, 100 minutes, 120 minutes, 150 minutes, 180 minutes, 200 minutes, 210 minutes, 230 minutes, 240 minutes, 250 minutes, 260 minutes, 280 minutes, 300 minutes, 320 minutes, 380 minutes, 390 minutes, 400 minutes, 420 minutes, 440 minutes, 460 minutes, 480 minutes, 500 minutes, 520 minutes, 550 minutes, or about or at least 600 minutes. The support can optionally be washed to remove non-EV materials, and solid support-bound EVs can be separated from the sample, e.g., by centrifugation, e.g., 10,000×g, 50,000×g, 100,000×g, or 200,000×g, or magnetization (e.g., exposure to a magnet), or other means appropriate to the solid surface, to isolate EVs.

In some instances, it may be desirable to separate the EVs from the solid support. To release solid support-bound EVs, various methods can be used. For example, a concentrated salt solution can be used to elute the EVs from the solid support. Non-limiting examples of salt that can be used include sodium chloride, potassium chloride, magnesium chloride, and calcium chloride. The salt solution can be concentrated at about 1 M, 1.25 M, 1.5 M, 1.75 M, 2 M, 2.25 M, 2.5 M, 2.75 M, or about 6 M. Skilled practitioners will be able to determine the amount of time needed to elute the EVs from the solid support, which will depend on the salt solution and concentration of the salt solution. For example, the solid support-bound EV can be incubated with 2 M NaCl in phosphate-buffered saline (pH 7.2) for about or at least 30 minutes, e.g., about or at least 40 minutes, 45 minutes, 50 minutes, 55 minutes, 60 minutes, 70 minutes, 80 minutes, 90 minutes, 100 minutes, 120 minutes, 150 minutes, 180 minutes, 200 minutes, 210 minutes, 230 minutes, 240 minutes, 250 minutes, 260 minutes, 280 minutes, 300 minutes, 320 minutes, 380 minutes, 390 minutes, 400 minutes, 420 minutes, 440 minutes, 460 minutes, 480 minutes, 500 minutes, 520 minutes, 550 minutes, or about or at least 600 minutes. The elution can be carried out at about 4° C., e.g., about 1° C., 2° C., 3° C., 5° C., 6° C., 7° C., 8° C., 10° C., 12° C., 14° C., 16° C., 18° C., 20° C., 22° C., 25° C., 26° C., 27° C., 28° C., 30° C., 32° C., 35° C., 38° C., or about 40° C. Alternatively, or in addition, the heparin-bound EV can be separated from the solid support by incubating the heparin-bound EV with heparinase at about 30° C., e.g., about 22° C., 25° C., 27° C., 29° C., 31° C., 33° C., 35° C., 37° C., or about 40° C., for about or at least 20 minutes, e.g., about or at least 25 minutes, 30 minutes, 35 minutes, 40 minutes, 45 minutes, 50 minutes, 55 minutes, 60 minutes, 70 minutes, 80 minutes, 90 minutes, 100 minutes, or about or at least 120 minutes. *Bacteroides* Heparinase I is commercially available from New England Biolabs (Ipswich, Mass.) and R&D Systems (Minneapolis, Minn.).

Therapeutic Agents

Isolated exosomes can be used for detecting biomarkers for diagnostic, therapy-related or prognostic methods to identify phenotypes, such as a condition or disease, for example, the stage or progression of a disease. Isolated exosomes can be used to profile physiological states or determine phenotypes of cells. Biomarkers or markers from isolated exosomes can be used to determine treatment regimens for diseases, conditions, disease stages, and stages of a condition, and can also be used to determine treatment efficacy. Markers from isolated exosomes can also be used to identify conditions of diseases of unknown origin such as described in WO 2010/056337, the entire contents of which are hereby incorporated by reference.

Isolated EVs can be loaded endogenously or exogenously with a therapeutic agent, e.g., a small interfering RNA (siRNA), miRNA, or an antisense oligonucleotide, a viral vector, or any agent that acts intracellularly, e.g., a therapeutic protein or a drug. Skilled practitioners would readily be able to use the isolated EVs as a vehicle to transport therapeutic agents. Examples are known in the art, for example, EV-mediated delivery of miRNA/siRNA has been described by Zhang et al., Biomaterials 35:4390-400, 2014; Alvarez-Erviti et al., Nat Biotechnol 29:341-5, 2011; and Ohno et al., Mol Ther 21:185-91, 2013. Use of EVs to transport virus vectors has been described by Maguire et al., Mol Ther 20:960-71, 2012; and Gyorgy et al., Biomaterials 35:7598-609, 2014. Further, delivery of drugs by EVs is disclosed by Sun et al., Mol Ther 18:1606-14, 2010.

Kits

The present disclosure also provides kits featuring heparin-coated solid supports described herein to isolate EVs. Such kits include at least one, e.g., two, three, five, or ten, solid supports described above. The kits can further include one or more solutions useful for performing the EV isolation methods described herein. For example, a kit may include a first solution comprising a buffer, e.g., PBS, preferably at a neutral pH, e.g., pH 7.2. Alternatively or in addition, the kit may include a second solution comprising high salt, e.g., 2 M or more concentrated salt, e.g., 1 M to 6 M or 2 M to 4 M, wherein the salt is NaCl, KCl, $MgCl_2$, $CaCl_2$, or other salt, in PBS (pH 7.2). Alternatively or in addition, the kit may include a third solution comprising heparinase. In some embodiments, all of the solutions are nuclease free and/or sterile. Preferably, the solutions are provided in liquid form in containers. Alternatively or in addition, the kit may include a filtration device, e.g., a 100 kDa molecular weight cutoff ultrafiltration device. In some instances, the kit may include one or more tubes, e.g., centrifuge or microcentrifuge tubes, e.g., a 50 mL centrifuge tube and/or a 1.5 mL microcentrifuge tube. In some embodiments, the 50 mL centrifuge tube and the 1.5 mL microcentrifuge tube are sterile and/or nuclease-free.

EXAMPLES

The invention is further described in the following examples, which do not limit the scope of the invention described in the claims.

Example 1

Extracellular Vesicles Bind to Heparin-Conjugated Agarose Beads

HEK293T cells were grown for 24 hours in 15-cm culture plates (~20 million cells/plate) in a total of 20 mL DMEM prepared with 5% EV-depleted fetal bovine serum (Skog et al., Nat Cell Biol 10:1470-1476, 2008). For each experiment, 60 mL of conditioned media (from 3 plates) was used to isolate EVs. The media was first centrifuged at 300×g for 10 minutes to remove any cells. The supernatant was then transferred to a clean tube and centrifuged again at 2000×g for 15 minutes to remove other debris. The supernatant was again transferred to a clean tube and filtered through a 0.8 µm filter (Millipore, Cork, IRL). At this point, 60 mL of filtered media was concentrated down to 3 mL by centrifuging at 1000×g for 10 minutes using a 100 kDa MWCO ultrafiltration device (AMICON® Ultra, Millipore). One mL of concentrated conditioned media each was used as input for each of the three isolation methods: heparin purification, ultracentrifugation, and EXOQUICK-TC™ (Systems Biosciences, Mountain View, Calif.; referred to in the present application as "EXOQUICK-TC™ kit").

Figure 1B:
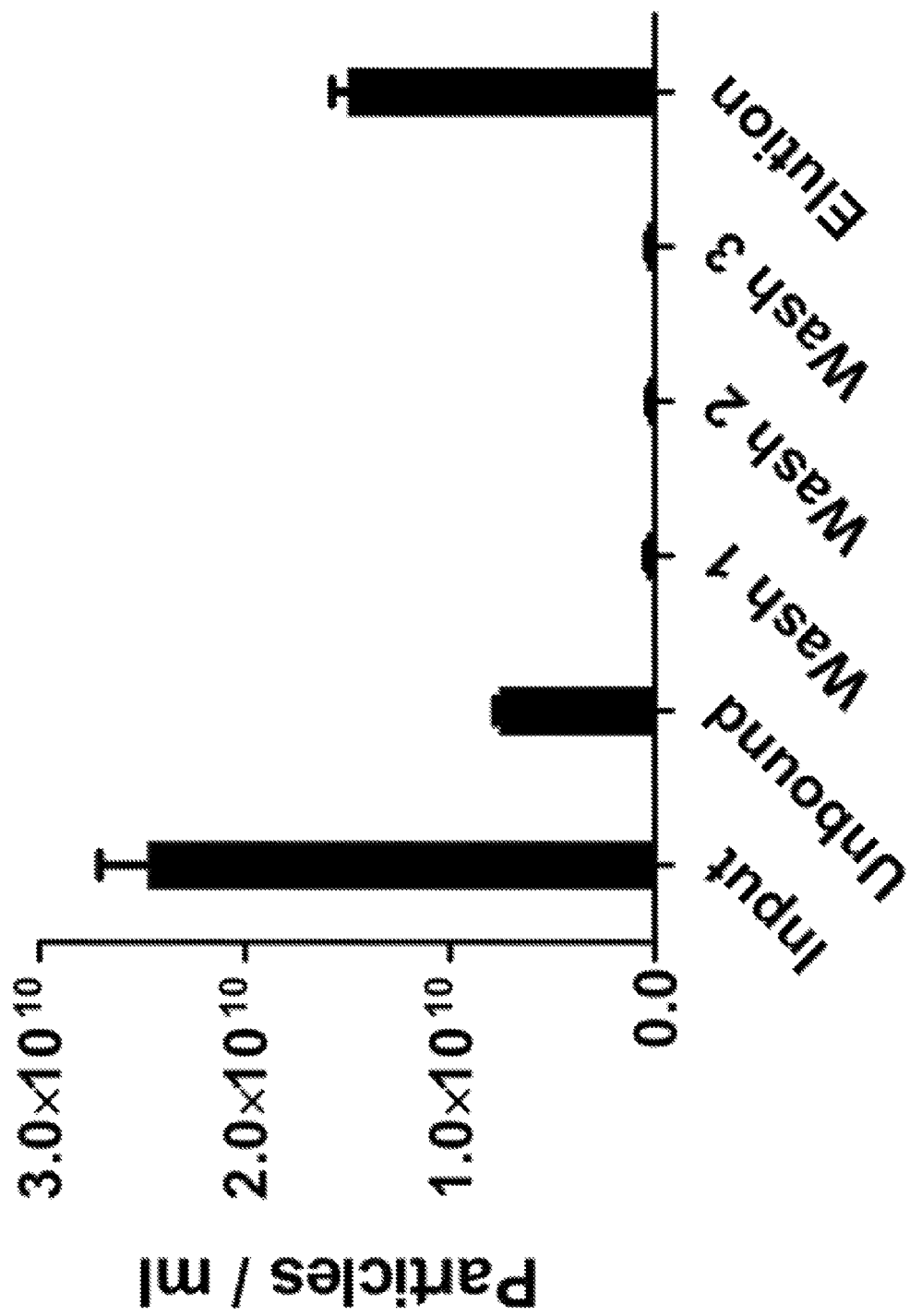
Figure 1C:
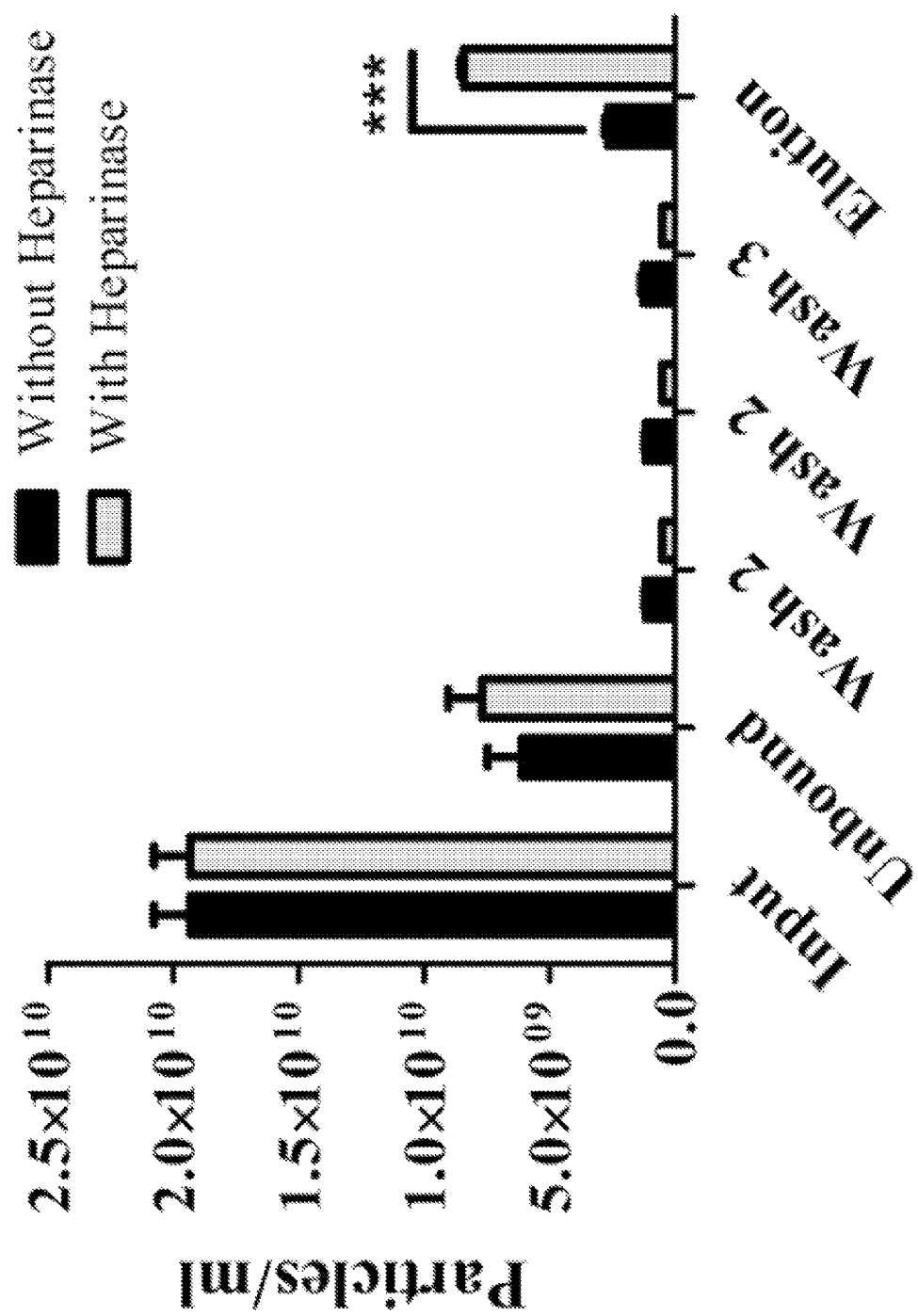
Figure 1D:
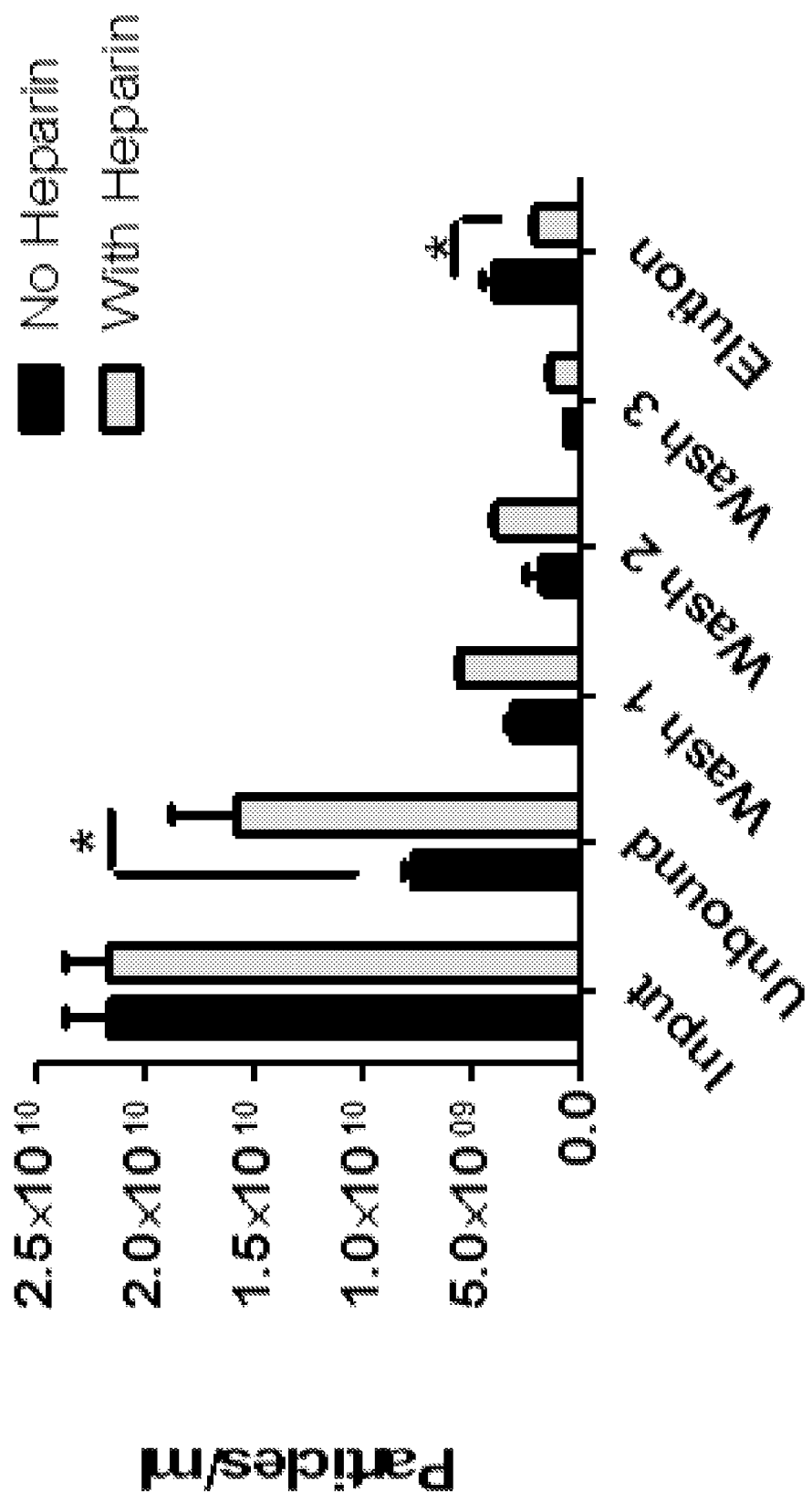
Figure 1E:
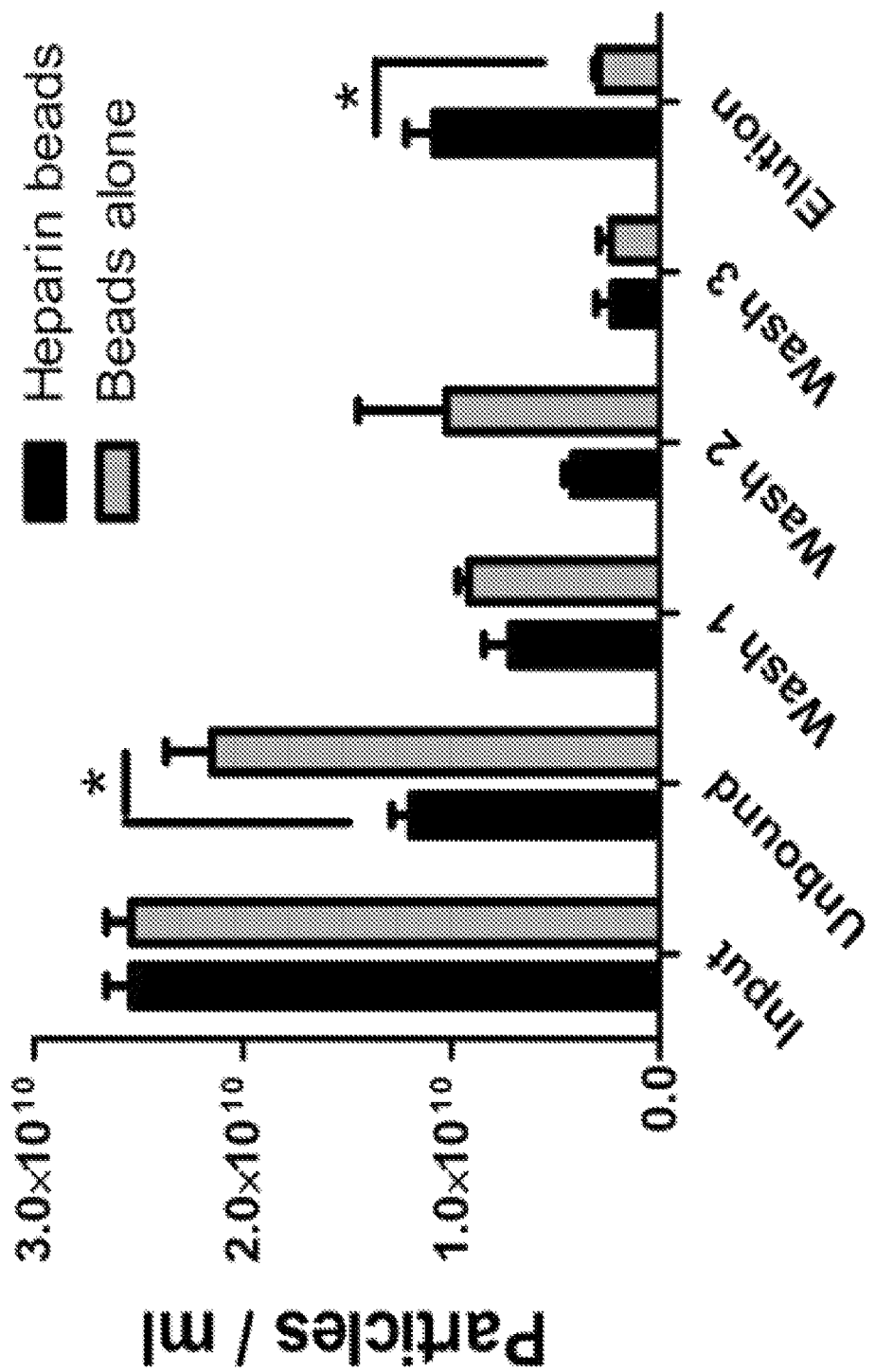

For heparin purification, one mL of AFFI-GEL® Heparin Gel (Bio-Rad, Hercules, Calif.) was washed twice with phosphate buffered saline (PBS), pH 7.2. A one mL sample of concentrated conditioned media was mixed with 1 mL of heparin-coated agarose beads and incubated on a tube rotator at 4° C. overnight. Beads were washed three times with PBS (pH 7.2) and eluted with 2 M NaCl in PBS overnight at 4° C. (FIG. 1A). Nanoparticle Tracking Analysis (NTA) was used to evaluate particle numbers in the samples (Webber et al., J Extracell Vesicles doi: 10.3402/jev.v2i0.19861, 2013) and 60% of the input EVs were recovered (FIG. 1B). To determine whether the binding of EVs to the beads was heparin-specific, EVs were mixed with heparin beads overnight at 4° C. and then performed three washes with PBS (pH 7.2) as in FIG. 1B. For elution, samples were either treated with control buffer or treated with heparinase to digest heparin, thereby releasing EVs from the agarose beads (FIG. 1C). The samples digested with heparinase had a significantly higher yield of EVs (p<0.00001) compared to mock-treated EV/heparin beads (no heparinase), as measured by NTA. The slight increase in the elution of mock-treated sample compared to the washes may be due to the incubation step at 30° C., required for heparinase to be active. Further evidence for a direct EV/heparin interaction was made by either mock-treating EVs or blocking EV binding to heparin beads using 0.1 mg/mL soluble heparin. EVs were mixed with heparin beads and isolated with one round of purification. The unbound and eluted fractions from round one were separately incubated with a fresh batch of heparin beads and a second round of purification was performed on these samples. Binding of EVs to heparin beads in the presence of excess soluble heparin was significantly less efficient when compared to mock-treated EVs (no soluble heparin) as there was significantly more unbound EVs in the sample pre-incubated with heparin than the mock-treated sample (p<0.04) (FIG. 1D). This block in binding resulted in 1.8-fold less EV in the elution step (p<0.01). As a final control for nonspecific binding of EVs to the agarose bead support matrix, an equal volume of concentrated 293T cell conditioned media was incubated with either heparin agarose beads or agarose beads without conjugated heparin. Next, the purification process for both samples was performed and all fractions were analyzed by NTA. EVs were mock-treated or incubated with 0.1 mg/mL soluble heparin for one hour at room temperature and then incubated with heparin beads overnight at 4° C. NaCl-eluted samples were analyzed using the NTA. There was a 1.8-fold higher amount of particles in the unbound fraction of control beads alone, compared to heparin beads (p<0.04; FIG. 1E). In contrast, a 3.6-fold lower number of particles were present in the elution fraction of EVs incubated with the control beads alone, compared with heparin beads (p<0.02). This result provides further evidence for a specific heparin/EV binding interaction.

Figure 1F:
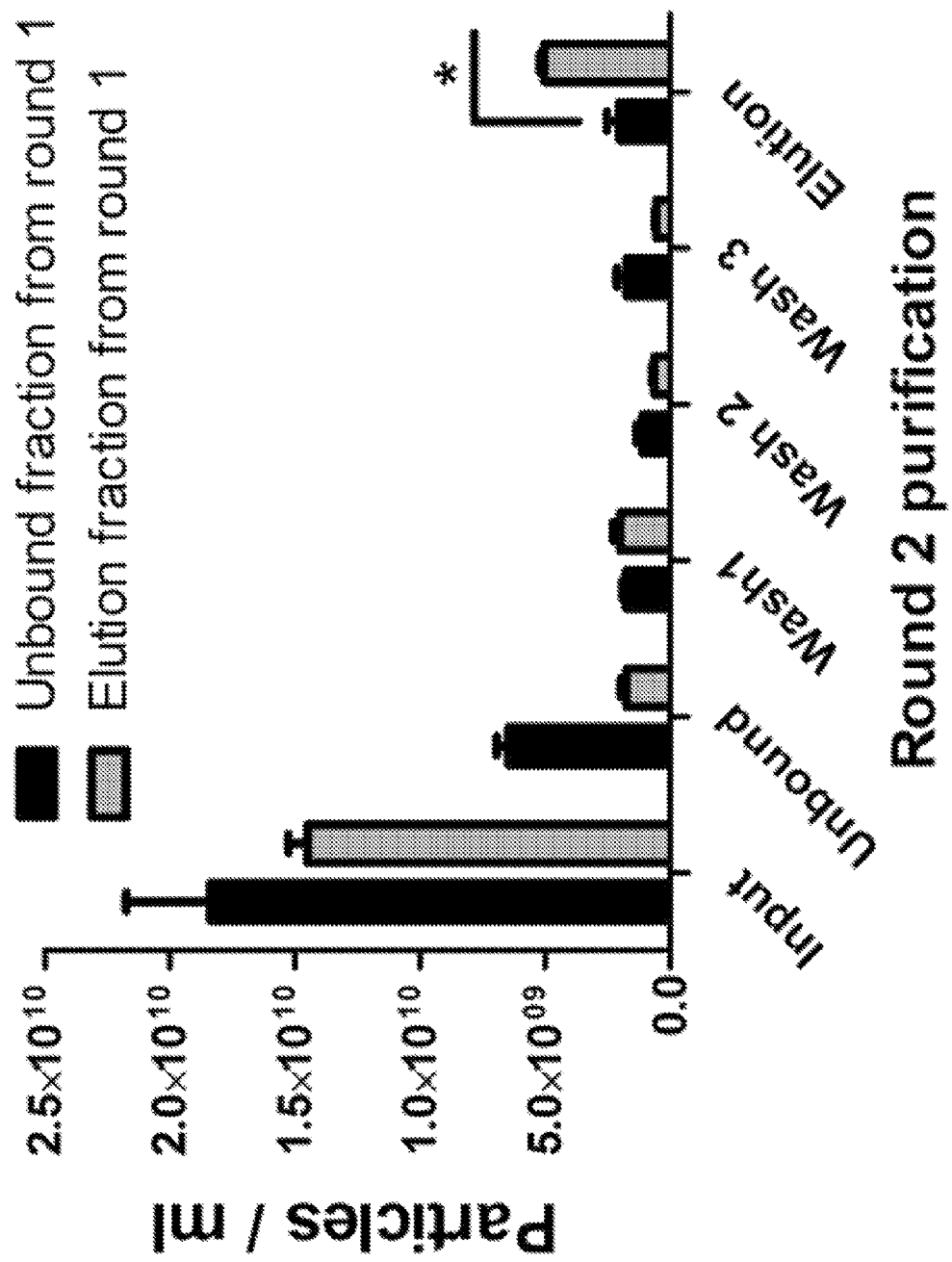
Figure 1G:
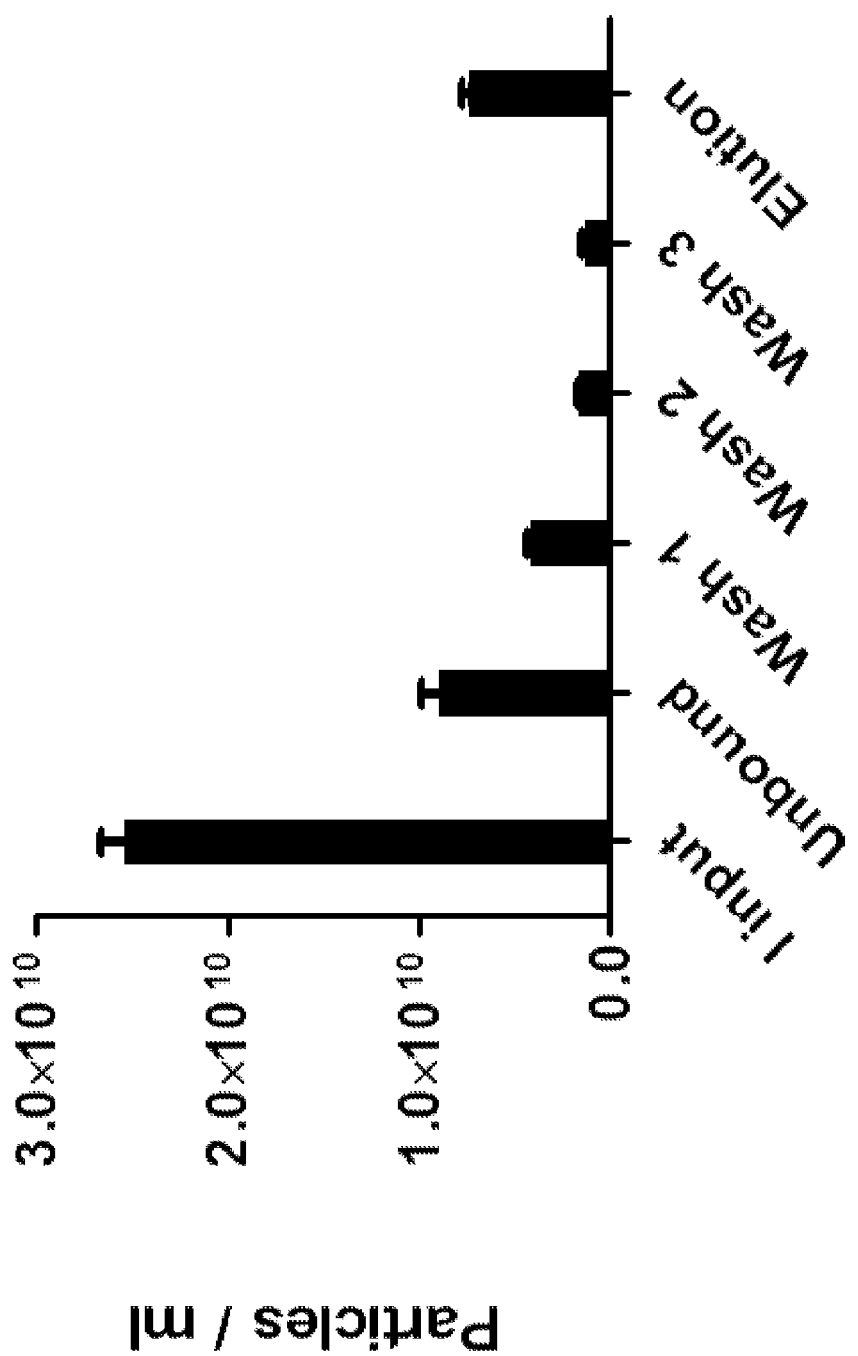
Figure 1H:
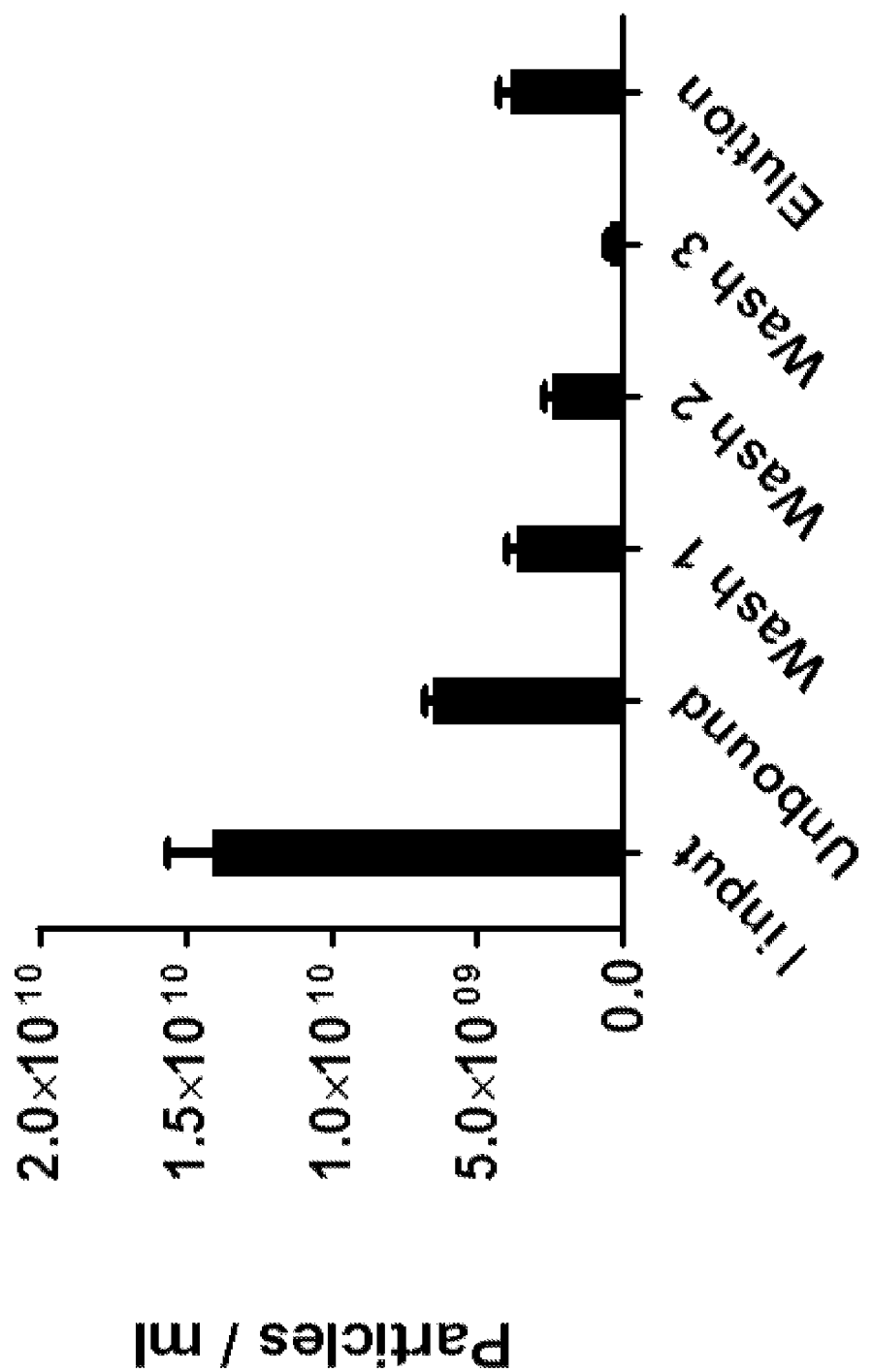

To test whether there are distinct populations of EVs that bind heparin better than others, 293T-derived EVs were incubated with heparin beads and all fractions (unbound, washes, elutions) were retained. Salt was removed from the eluted fraction by diafiltration. Next, the unbound fraction (i.e., did not bind heparin beads on round 1 purification) or the eluted fraction was incubated with a subsequent batch of heparin beads. For each sample, washes and elutions were performed, and particles were counted by NTA. Interestingly, the unbound fraction from purification round 1 gave 35% of unbound particles in round 2, while the round 1 eluted samples had only 12% in the unbound fraction in round 2 (p<0.003; FIG. 1F). On the other hand, there was a 2.5-fold higher particle count in the round 2 elution from the round 1 eluted sample compared to round 2 elution with the round 1 unbound sample (p<0.004; FIG. 1F). This result suggests that the 293T EVs are comprised of a mixed pool with some binding more strongly to heparin than others. EVs from U87 cells (FIG. 1G) as well as HUVEC cells (FIG. 1H) could be purified using heparin beads, as determined by NTA counts with 30% and 28% recovery, respectively, following overnight high salt elution at 4° C.

Example 2

Figure 2A:
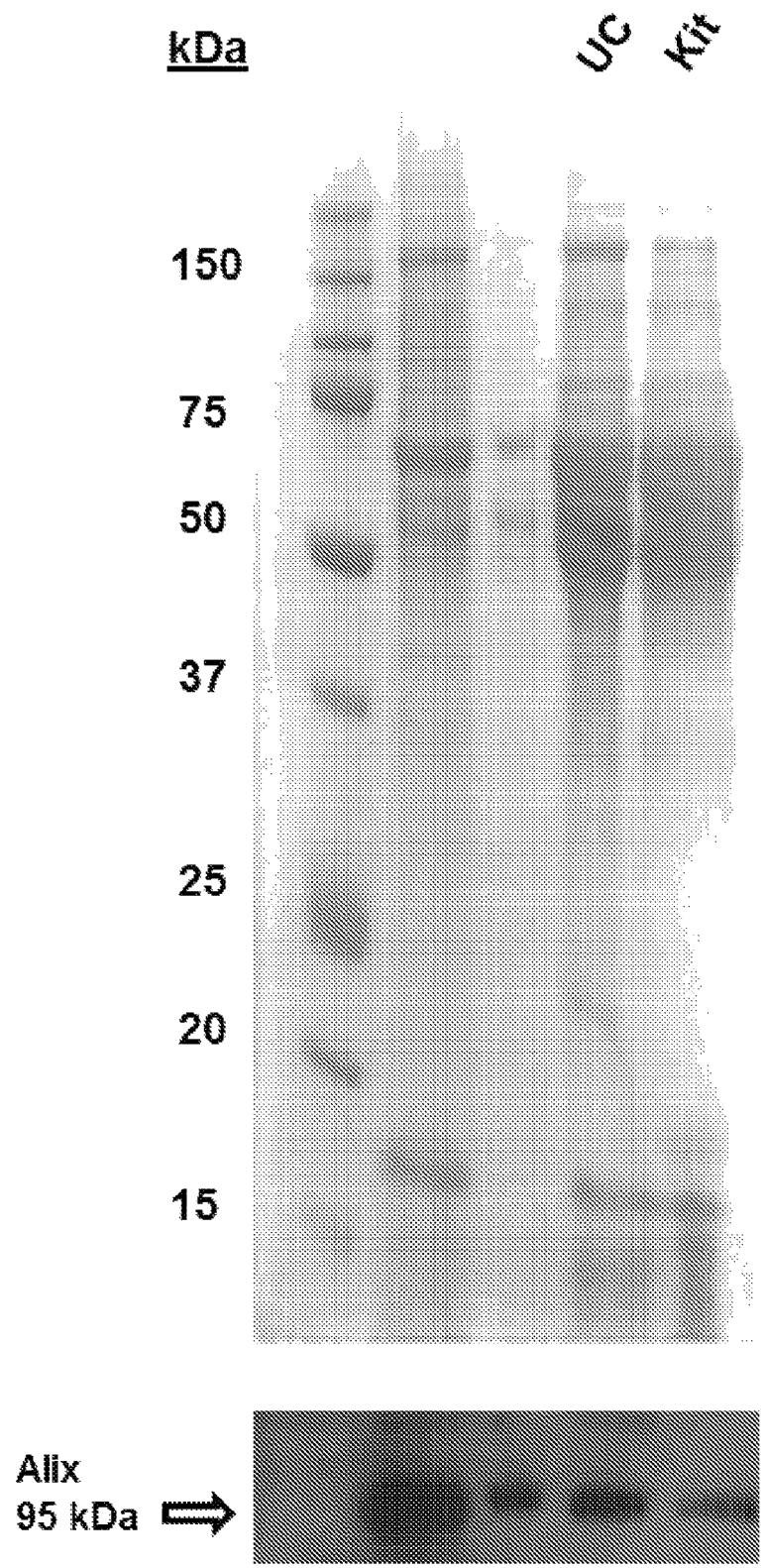
FIGS. 2A to 2D are a series of four panels characterizing total proteins and EV markers from heparin-purified (HeP), sucrose gradient (SuC) ultracentrifuged (UC), and EXOQUICK-TC™ commercial kit (Kit)-isolated EVs.
Figure 2B:
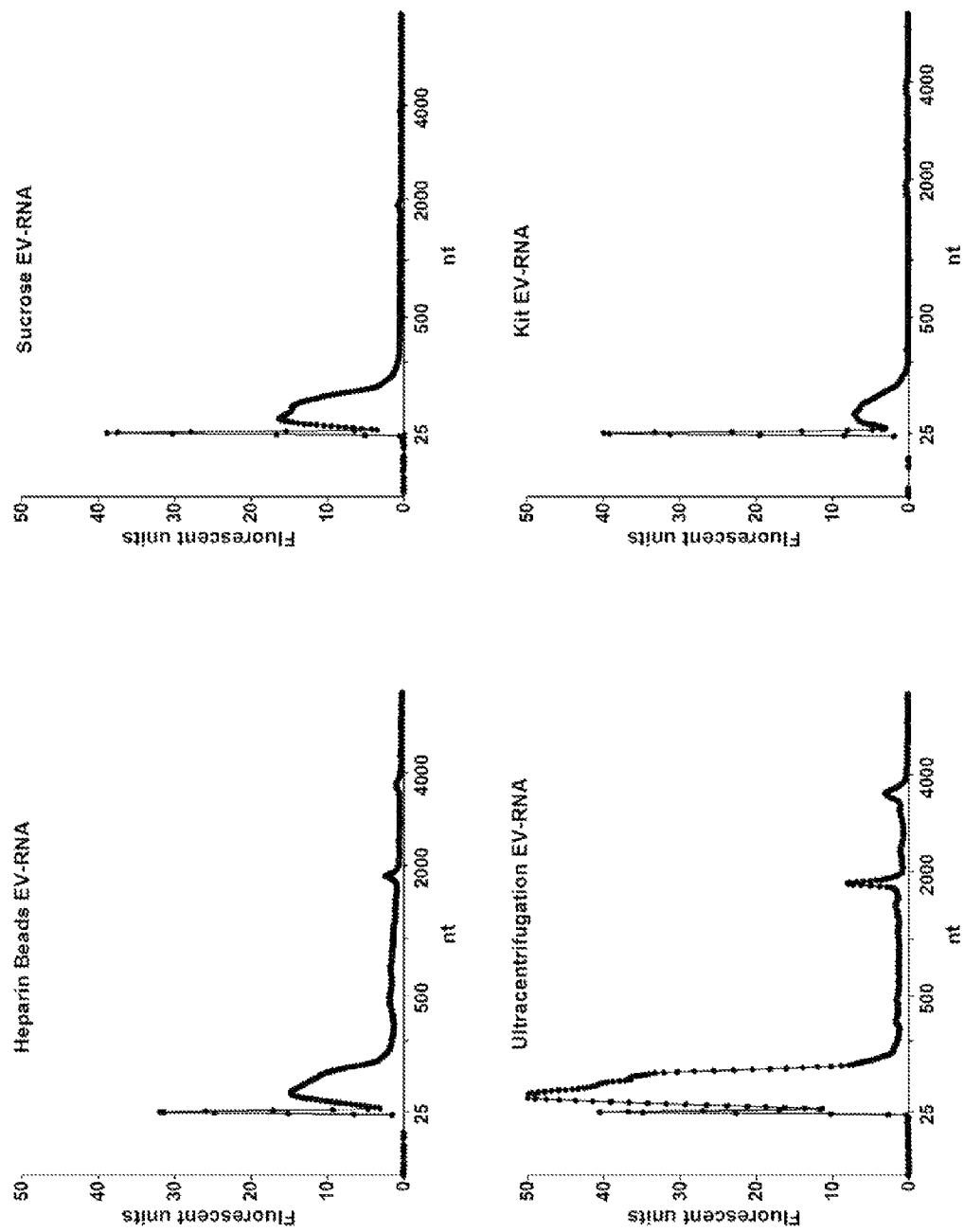
Figure 2C:
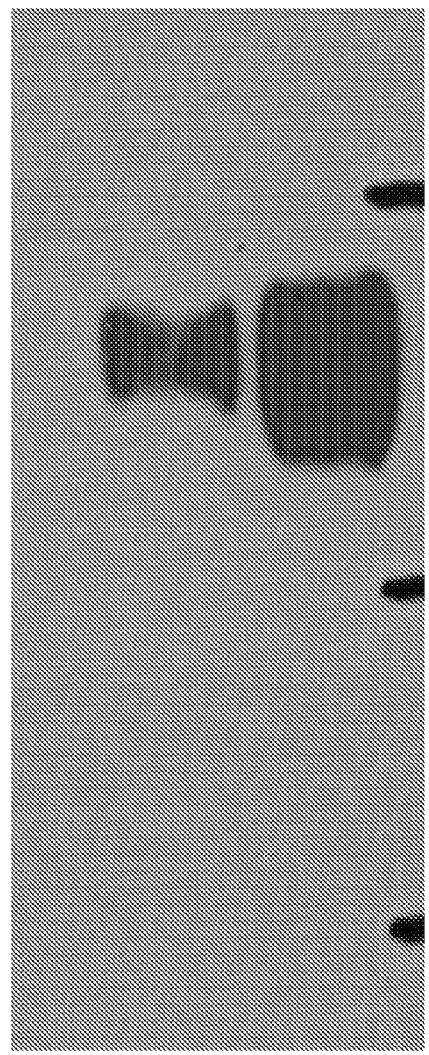

Heparin-Purified EVs Contain EV-Associated Biomarkers and Lower Levels of a Contaminating Protein One mL of concentrated, conditioned media was purified by heparin-coated beads (HeP), UC, sucrose gradient (SuC), or the commercial EXOQUICK-TC™ kit. In two separate preparations from 293T cells, EVs isolated with each of these methods had EVs counted using NTA. The EV number ($2.1 \times 10^{10}$ for each lane) was used to normalize protein loading on the SDS-PAGE gel. Normalization was based either on EV counts (FIG. 2A) or on total yield of RNA (FIG. 2B). Each sample was split into two fractions: fraction one was used for SDS-PAGE gel electrophoresis and Coomassie staining to visualize total protein associated with each purification method (FIG. 2A, top panel). The second fraction was used for Western blot analysis of the EV-associated protein, Alix (FIG. 2A, bottom panel). All samples were DNAse treated prior to nucleic acid extraction. Strong bands were observed in FIG. 2A for UC and EXO-QUICK-TC™ kit-isolated EVs were between 50 and 75 kDa, while weaker bands in this size range were seen for heparin-isolated and sucrose gradient purified EVs. As BSA (MW 69 kDa) has been reported to co-purify with EVs (Webber et al., J Extracell Vesicles doi: 10.3402/jev.v2i0.19861, 2013), an anti-BSA immunoblot was performed and a broad, intense band around 69 kDa, was detected in 293T ultracentrifuged EVs following SDS-gel electrophoresis and immunoblotting with an anti-BSA antibody. UC or heparin-isolated EV samples were normalized for vesicle counts by NTA and subjected to SDS-PAGE. A band with less intensity was also observed in the heparin bead-purified sample (FIG. 2C). These BSA bands are likely the intense bands seen by Coomassie staining in FIG. 2A (top panel). Blotting for Alix revealed an intense band of the expected molecular weight for all samples (FIG. 2A, bottom panel). Heparin-purified EVs from 1 mL of concentrated conditioned media (starting volume 20 mL) were eluted overnight in 1 mL of 2 M NaCl at 4° C., ultracentrifuged at 100,000×g for 90 minutes, and lysed in 700 μL of QIAZOL lysis buffer. The RNA yields and profiles of the EV-RNA in heparin-purified samples were evaluated and compared to sucrose-, UC-, and EXOQUICK-TC™ kit-isolated samples (Table 1). EV-RNA yield was quite similar among the different purification methods (Table 1). All methods displayed a peak in the small RNA region suggesting the presence of small RNAs/miRNA species as well as larger RNA species such as ribosomal RNAs (FIG. 2B). Samples in the four different isolation methods were frozen at −80° C. and stored at 4° C. in the same fashion to account for RNA stability under different storage conditions.

TABLE 1

Yield of RNA.

| Isolation Method | RNA (ng) |
| --- | --- |
| HeP | 16 |
| SuC | 10 |
| UC | 17 |
| EXOQUICK-TC™ Kit | 12 |

Figure 2D:
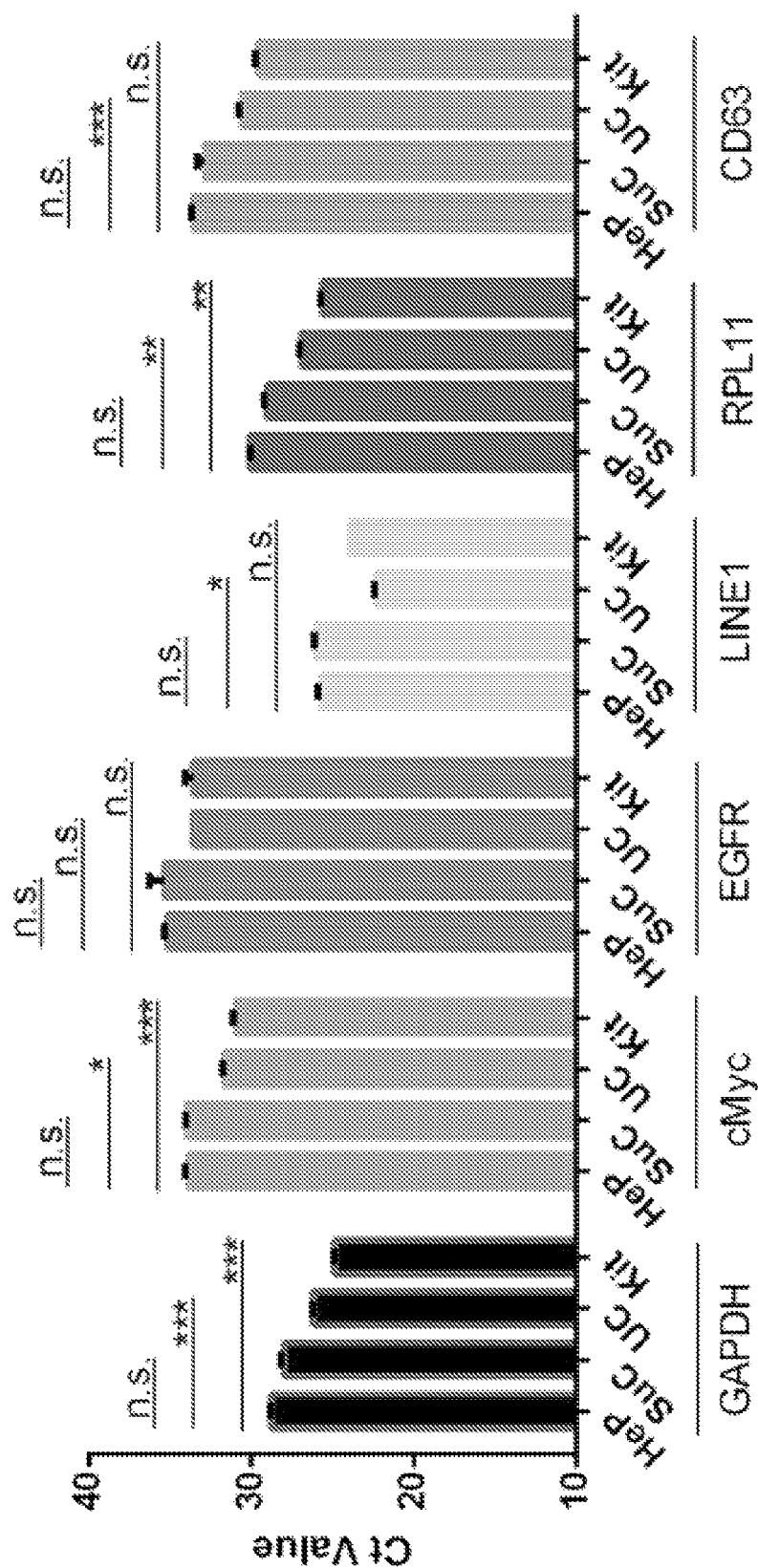

Next, qRT-PCR was performed on the RNA (DNAse treated) isolated from these EV samples and a variety of mRNA (GAPDH, RPL11, EGFR, LINE1, CD63, and cMyc) were found within heparin-purified EVs, similar to the other isolation methods (FIG. 2D). qRT-PCR on the RNA showed that abundant cellular RNA species, such as GAPDH and RPL11, are significantly higher in UC and commercial EXOQUICK-TC™ kit samples indicating they may be present in vesicles, particles, or aggregates that do not bind to heparin. Both of these abundant genes were recovered at similar levels between sucrose gradients and heparin-coated beads. Interestingly, the EGFR and LINE1 mRNAs were recovered at similar levels among all different EV isolation methods. This strongly suggests that the quality of purification may be more important than abundance of EVs so selective binding of EVs from biological fluids may improve biomarker assays detection and efficiency. CD63 mRNA and cMyc were recovered at slightly higher efficiency with heparin, as compared to using UC or the commercial EXO-QUICK-TC™ kit. Overall, the sucrose gradient and heparin-purified EVs contained similar amounts of all genes investigated, but the latter method is less laborious and does not require expensive laboratory equipment. No signal was detected in samples that did not include a reverse-transcriptase step, excluding the possibility of DNA contamination contributing to the Ct values detected.

Figure 3:
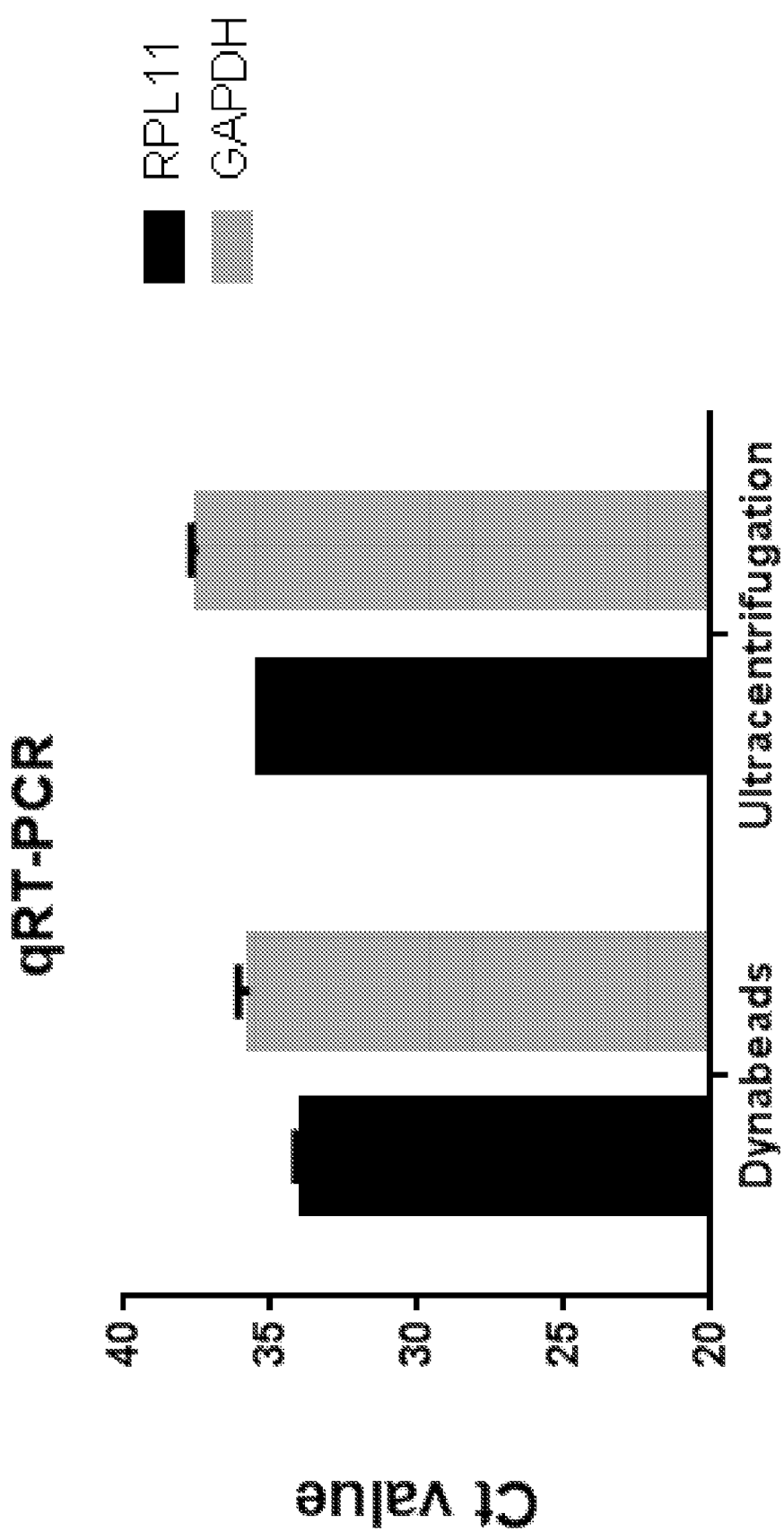
FIG. 3 is a bar graph depicting mRNA quantification of heparin-isolated and ultracentrifuged human blood plasma derived EVs. Data is shown in Ct values (lower Ct means higher levels).

Example 3 mRNA Quantification in Heparin Bead Isolated and Ultracentrifuged Plasma Samples Plasma samples from healthy donors were stored at −80° C. until analysis. One mL of plasma from healthy controls was thawed on ice, added to a 100 kDa Amicon filter (Millipore), washed with PBS buffer, and used for heparin-affinity isolation and ultracentrifugation. Half of the washed EVs was added to biotin heparin-streptavidin-coated DYNABEADS® MYONE™ Streptavidin C1 (Life Technologies, Grand Island, N.Y.) and incubated on a rotator overnight at 4° C. to allow binding. The other half of the washed EVs was stored at 4° C. until day two and then ultracentrifuged at 100,000×g to collect EVs. RNA was extracted from both samples using a miRNeasy kit (Qiagen)

and analyzed by qRT-PCR. GAPDH and RPL11 mRNA were detected in heparin-bead isolated EVs as well as EVs isolated by ultracentrifugation (FIG. 3). Both mRNAs tended to be at higher levels in the heparin-isolated EVs. Streptavidin-coated magnetic DYNABEADS (Life Technologies, Grand Island, N.Y.) bound to biotinylated heparin are very robust in isolating a pure population EVs from biological fluids.

Example 4

Electron Microscopic Analysis of Isolated Extracellular Vesicles

To directly examine the morphology of heparin-purified EVs in comparison to other methods of EV isolation, EVs were examined by transmission electron microscopy (TEM). Resuspended pellets from UC EVs showed an expected round-shaped vesicles with a size range of approximately 30-200 nm and some clumping of vesicles (FIG. 4A). On the other hand, the TEM profile of vesicles isolated with the commercial EXOQUICK-TC™ kit was very uniform, containing small round particles (~30 to 50 nm) that appeared to be connected to each other over a large network (FIG. 4B). EV-looking structures were difficult to identify. In contrast, EVs isolated using heparin-coated beads had a size distribution similar to that of the UC samples (FIG. 4C). Importantly, the heparin-isolated EVs were evenly dispersed across the grid, which contrasted with the UC purified EVs, where more clumping was observed (FIG. 4C). Arrows point to large EVs (~50 to 100 nm) and arrowheads point to small EVs (<~50 nm). It is unclear if the structures observed in the commercial EXOQUICK-TC™ kit are EVs or if they are components of the proprietary precipitating reagent.

Example 5

Heparin-Isolated Extracellular Vesicles are Internalized by U87 Cells 293T-derived EVs from one mL of concentrated conditioned media were isolated by heparin affinity or UC and labeled with PKH67 green-fluorescent lipid dye to visualize uptake by U87 cells. After 30 minutes of incubation at 37° C., cells were fixed in formaldehyde, nuclei stained with Hoescht and imaged using a confocal fluorescence microscope. After 30 minutes of incubation with U87 cells, EVs from both isolation methods enter U87 cells (FIGS. 5A and 5B), demonstrating that EVs isolated by heparin retain structural integrity. Note the punctate fluorescent structures inside cells, which are characteristic of labeled EVs in endocytic structures.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of isolating an extracellular vesicle (EV), the method comprising:
providing a sample comprising an EV;
contacting the sample with a heparin-coated solid support under conditions that allow the solid support to bind to the EV; and
separating the solid support-bound EV from the sample, thereby isolating the EV from the sample.

2. The method of claim 1, wherein the sample comprises biological fluid.

3. The method of claim 1, wherein the sample comprises human biological fluid.

4. The method of claim 1, wherein the sample comprises urine, mucus, saliva, tears, blood, serum, plasma, sputum, cerebrospinal fluid, ascites fluid, semen, lymph fluid, airway fluid, intestinal fluid, breast milk, amniotic fluid, or any combination thereof.

5. The method of claim 1, wherein the sample comprises cell culture medium.

6. The method of claim 1, wherein the solid support is a bead.

7. The method of claim 1, wherein the solid support is selected from the group consisting of an agarose bead, a magnetic bead, a silica bead, a polystyrene plate, a polystyrene bead, a glass bead, a cellulose bead, a heparin-conjugated affinity chromatography column, or any combination thereof.

8. The method of claim 1, wherein the sample is contacted with the heparin coated solid support at 4° C. for at least 30 minutes.

9. The method of claim 1, wherein the solid support-bound EV is separated from the sample by centrifugation, elution, or magnetization.

10. The method of claim 1, wherein the solid support-bound EV is released from the solid support by incubating the solid support-bound EV with salt.

11. The method of claim 1, wherein the solid support-bound EV is released from the solid support by incubating the solid support-bound EV with 2 M sodium chloride.

12. The method of claim 10, wherein the incubating is performed at 4° C. for at least 30 minutes.

13. The method of claim 1, wherein the solid support-bound EV is released from the solid support by incubating the solid support-bound EV with heparinase.

14. A kit for use in performing the method of claim 1.

15. The method of claim 1, the method further comprising loading the isolated EV with a therapeutic agent.

16. The method of claim 15, wherein the therapeutic agent is a siRNA, a miRNA, an antisense oligonucleotide, a polypeptide, a viral vector, or a drug.

* * * * *